United States Patent [19]

Sanchez

[11] Patent Number: 5,837,782

[45] Date of Patent: Nov. 17, 1998

[54] BIS(MONO-AND-DIPEROXYOXALATES) DERIVED FROM DIHYDROPEROXIDES AND ALKYL AND ALKYLPEROXY HALOOXALATES

[75] Inventor: Jose Sanchez, Grand Island, N.Y.

[73] Assignee: Elf Atochem North America, Inc., Philadelphia, Pa.

[21] Appl. No.: 947,533

[22] Filed: Oct. 10, 1997

Related U.S. Application Data

[60] Provisional application No. 60/034,528 Dec. 30, 1996.

[51] Int. Cl.$^6$ .......................... C08F 20/22; C07C 69/67; C07C 331/04; C07G 63/91

[52] U.S. Cl. .......................... 525/447; 560/176; 560/302; 525/27; 526/231; 526/232; 526/232.3; 526/232.5

[58] Field of Search .................... 560/176, 302; 525/447, 27; 526/231, 232, 232.3, 232.5

[56] References Cited

U.S. PATENT DOCUMENTS

| | | | |
|---|---|---|---|
| 3,117,166 | 1/1964 | Harrison et al. | 260/610 |
| 3,264,274 | 8/1966 | Leveskis | 260/80 |
| 3,297,738 | 1/1967 | Mageli et al. | 260/463 |
| 3,574,696 | 4/1971 | Friedman et al. | 260/453 |
| 3,624,123 | 11/1971 | Lewis et al. | 260/453 |
| 4,859,794 | 8/1989 | Lundin et al. | 560/302 |

FOREIGN PATENT DOCUMENTS

| | | |
|---|---|---|
| 0049966 A1 | 4/1982 | European Pat. Off. . |
| 0095860 A2 | 7/1983 | European Pat. Off. . |
| 0 500 624 B1 | 5/1991 | European Pat. Off. . |

OTHER PUBLICATIONS

Journal American Chemical Society (82) 1960 P.D. Bartlett, R. R. Hiatt pp. 1762–1768.
Journal American Chemical Society (82) 1960 L.S. Silbert & D. Swern pp. 1769–1773.
Journal American Chemical Society (35) 1970 C. Walling & J. A. McGuinness pp. 1223–1226.
Journal American Chemical Society (99) 1977 W. Adam & J. Sanabia pp. 2735–2739.
J. Macromol Sci A17 (1) 1982 P. Griffiths, E. Rizzardo, D. Solomon pp. 45–50.
Journal f. prakt. Chemie 324 (4) 1982 J. A. Barth, Leipzig pp. 588–595.

*Primary Examiner*—Johann Richter
*Assistant Examiner*—Dominic Keating
*Attorney, Agent, or Firm*—Stanley A. Marcus; Royal E. Bright

[57] ABSTRACT

A novel bis(mono- or diperoxyoxalate) composition of Structure A,

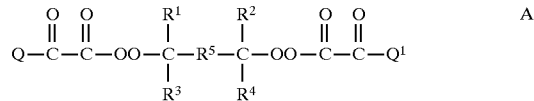

and use of the novel bis(mono- or diperoxyoxalate) composition as an initiators for curing of unsaturated polyester resins and for polymerizing ethylenically unsaturated monomers are disclosed.

12 Claims, No Drawings

BIS(MONO-AND-DIPEROXYOXALATES) DERIVED FROM DIHYDROPEROXIDES AND ALKYL AND ALKYLPEROXY HALOOXALATES

This Application claims priority from Provisional Application S/N 60/034,528, filed Dec. 30, 1996.

BACKGROUND OF THE INVENTION

1. Field of the Invention

This invention relates to new and novel compositions of matter classified in the art of chemistry as bis(mono- and diperoxyoxalates) of Structure A that are preparable by reaction of

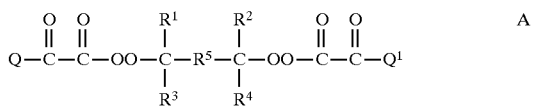

[The definitions of Q, $Q^1$, $R^1$, $R^2$, $R^3$, $R^4$, and $R^5$ are given in the SUMMARY OF THE INVENTION] dihydroperoxides, such as 2,5-dimethyl-2,5-dihydroperoxyhexane and 2,5-dimethyl-2,5-dihydroperoxy-3-hexyne, with alkyl and alky-Lperoxy halooxalates, such as ethyl chlorooxalate and t-butylperoxy chlorooxalate, in the presence of inorganic or organic bases, as well as processes for their preparation and use. The compositions of the invention possess inherent applied use characteristics rendering them suitable as synthetic intermediates and as initiators for polymerizing ethylenically unsaturated monomers and for curing of unsaturated polyester resin compositions.

There is a need in the polymer industries for efficient, free-radical initiators for polymerizing ethylenically unsaturated monomers at lower temperatures in order to attain higher molecular weight polymers having improved tensile and other mechanical properties and/or to increase rates of polymerizations in order to produce current polymers at higher rates of production, thus lowering production costs. In the case of the latter scenario, the more efficient free-radical initiators enable polymer producers to increase productivity without need to build new and expensive production facilities. There also is a need in the polyester industry for free-radical initiators that cure unsaturated polyester resins faster and/or at lower temperatures. The novel bis (mono- and diperoxyoxalate) compositions of Structure A and of this invention are capable of satisfying these polymer industry needs.

2. Description of the Prior Art

P. D. Bartlett, et al. (*J. Am. Chem. Soc.*, 82, 1762–8, 1960) described the decomposition kinetics of di-t-butyl diperoxyoxalate (CAS RN 1876-22-2) in solution and found its half-life at 60° C. in benzene to be 6.8 minutes. In a subsequent paper P. D. Bartlett and R. E. Pincock (*J. Am. Chem. Soc.*, 82, 1769–73, 1960) disclosed the decomposition kinetics of di-t-butyl diperoxyoxalate and several OO-t-butyl O-alkyl monoperoxyoxalates including OO-t-butyl O-ethyl monoperoxyoxalate and OO-t-butyl O-benzyl monoperoxyoxalate. Based on the data provided in this reference the 10 hour half-life temperatures (i.e., the temperature at which 50% of the peroxide is decomposed in 10 hours) were calculated to be 26° C., 39° C. and 41° C., respectively, for the above peroxyoxalates. Thus, di-t-alkyl diperoxyoxalates have 10 hour half-life temperatures of about 25° C. whereas OO-t-alkyl O-alkyl monoperoxyoxalates have 10 hour half-life temperatures of about 40° C. A bis(monoperoxy-oxalate) of the instant invention, i.e., 2,5-dimethyl-2,5-di(isobornyloxycarbonylcarbonylperoxy) hexane (I-4),

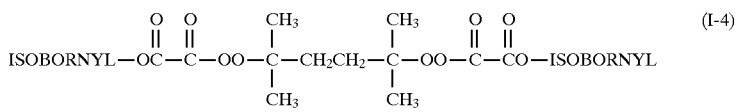

was found to have a 10 hour half-life temperature of 20° C. in trichloroethylene. Hence, the novel bis(mono-and diperoxyoxalates) of the instant invention are significantly more active than the OO-t-alkhl O-alkyl monoperoxyoxalates of the art.

R. A. Sheldon and J. K. Kochi (*J. Org. Chlem.*, 35 1223–6, 1970) reported on the rates of decompositions of various di-t-alkyl diperoxyoxalates of the structure,

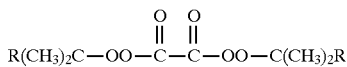

(where R is methyl, ethyl, isopropyl and benzyl) The data were consistent with those of Bartlett.

W. Adam and J. Sanabia (*J. Am. Chem. Soc.*, 99, 2735–9, 1977) describe the synthesis of a cyclic diperoxyoxalate, 7,7,10,10-tetramethyl-1,2,5,6-tetraoxa-3,4-dioxocyclodecane,

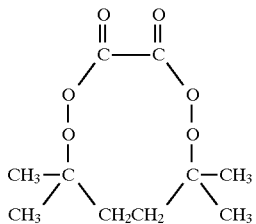

from oxalyl chloride and 2,5-dimethyl-2,5-dihydroperoxyhexane in the presence of pyridine. Based on the data provided in this reference the 10 hour half-life temperature of the cyclic diperoxyoxalate was calculated to be about 80° C. It should be noted that the peroxide of Adam and Sanabia is a cyclic diperoxyoxalate not a bis (monoperoxyoxalate).

P. G. Griffiths, et al. [*J. Macromol. Scdi., Chem.*, A17(1), 45–50, 1982] disclose polymerizations of alkyl methacrylates with di-t-butyl diperoxyoxalate.

European Patent Application No. EP 0049966 A1 (Apr. 21, 1982, to ICI Australia, Ltd.) discloses a process for polymerizing vinyl chloride (VCl) monomer using as an initiator, di-t-butyl diperoxyoxalate.

M. Schulz, et al. [*J. Prakt. Chem.*, 321(4), 589–95, 1982] describe the synthesis and the thermolysis of azobis(isobutyl t-butyl peroxyoxalate),

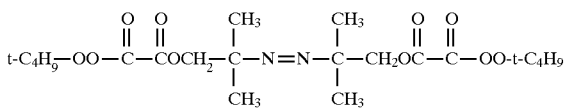
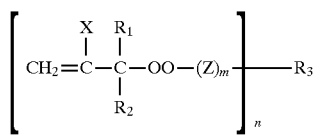

a sequentially decomposing azo-peroxide.

European Patent Application No. EP 0095860 A2 (Dec. 7, 1983, to ICI Australia, Ltd.) discloses a process for polymerizing VCl monomer using as an initiator a diester of monoperoxyoxalic acid of the structure,

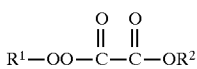

where $R^1$ is a secondary or tertiary alkyl group, or a benzyl or a substituted benzyl group and $R^2$ is a secondary or tertiary alkyl group, or a benzyl or a substituted benzyl group. Also disclosed in this patent application are t-alkylperoxy chlorooxalates of the structure,

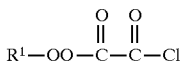

These intermediates are used for preparations of the diesters of monoperoxyoxalic acid.

U.S. Pat. No. 4,859,794 (Aug. 22, 1989, to Berol Nobel Nacka AB) discloses dialkyl esters of monoperoxyoxalic acid of structure,

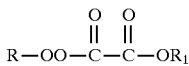

(where $R=C_{4-10}$ t-alkyl and $R_1=C_{18-28}$ primary alkyl) for example, OO-t-butyl O-docosyl monoperoxyoxalate, useful for initiating polymerization of VCl and other monomers.

Japanese Patent Applications JP 63/248806 (Oct. 17, 1988, to NOFCO) and Japanese Patent 63,/254110 (Oct. 20, 1988, to NOFCO) disclose OO-t-alkyl O-alkyl monoperoxyoxalates of the structure,

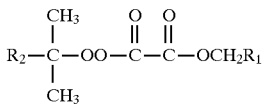

[where $R_1$=H, alkyl and $R_2=C_{1-7}$ alkyl, (substituted) $C_6H_5$, etc.]

as initiators for producing VCl polymers having low odor and color.

European Patent Specification No. 0500624 B1 (Jul. 12, 1994, to Akzo Nobel N.V.) disclosed allyl peroxide chain transfer agents of the structure, where n is an integer of 1–4, $R_1$ and $R_2$ may be the same or different and are selected from hydrogen or lower alkyl, $R_3$ is selected from alkyl of 4–8 carbons, alkenyl of 5–18 carbons, etc., X is an activating group capable of enhancing the reactivity of the olefinic unsaturation towards free-radical addition, m is 0 or 1 and Z is selected from the structures, $$-\overset{O}{\underset{\|}{C}}-, \quad -\overset{O}{\underset{\|}{C}}-O-, \quad -\overset{O}{\underset{\|}{C}}-\overset{O}{\underset{\|}{C}}-O-$$

If Z is the latter structure then the compounds of European Patent Specification No. 0500624 B1 can be monoperoxyoxalates. However, the compositions of 0500624 B1 do not disclose the compositions of the instant invention since the peroxides of Structure A are not allyl peroxides nor does the instant invention cover the compositions of 0500624 B1. It should be noted that no monoperoxyoxalates are included in the list of peroxides on pages 5, 7 and 8 or in the preparative examples of 0500624 B1.

As a whole, the above art does not disclose the bis(mono- and diperoxyoxalate) compositions of Structure A.

U.S. Pat. No. 3,117,166 (Jan. 7, 1964, to Wallace & Tiernan) discloses diperoxyester derivatives of 2,5-dimethyl-2,5-dihydroperoxyhexane such as 2,5-dimethyl-2,5-di(acetylperoxy)hexane, 2,5-dimethyl-2,5-di(2-carboxybenzoylperoxy)hexane and 2,5-dimethyl-2,5-di (ethoxycarbonylperoxy)hexane.

U.S. Pat. No. 3,297,738 (Jan. 10, 1967, to Wallace & Tiernan) discloses acetylenic bis(monoperoxycarbonates) derived from alkyl chloroformates and dihydroperoxides containing —C≡C— and —C≡C—C≡C— moieties, such as 2,5-dimethyl-2,5-di(ethoxycarbonylperoxy)-3-hexyne, 3,6-dimethyl-3,6-di(ethoxycarbonylperoxy)-4-octyne and 2,7-dimethyl-2,7-di(ethoxycarbonylperoxy)-3,5-octadiyne.

U.S. Pat. No. 3,264,274 (Aug. 2, 1966, to Witco Chemical Corporation) discloses diperoxyesters of the structure,

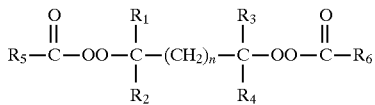

where n is 1 to 5, $R_1$, $R_2$, $R_3$ and $R_4$ are selected from hydrogen and alkyl radicals of 1 to 5 carbons and $R_5$ and $R_6$ are alkyl radicals, branched in the of α-position, of 3 to 20 carbons.

U.S. Pat. No. 3,574,696 (Apr. 13, 1971, to Witco Chemical Corporation) discloses acetylenic diperoxyesters of the structure,

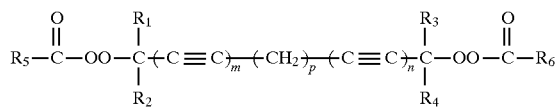

where p is 1 to 7, m and n are 0 or 1, $R_1$, $R_2$, $R_3$ and $R_4$ are selected from lower alkyl radicals of 1 to 5 carbons and $R_5$ and $R_6$ are alkyl radicals of 1 to 12 carbons, with the proviso

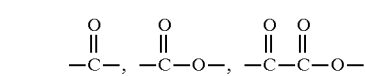

that $R_5$ and $R_6$ are primary or secondary alkyl radicals. The sum of m and n must be at least 1.

U.S. Pat. N0. 3,624,123 (Nov. 30, 1971, to Witco Chemical Corporation) discloses bis(neoperoxyesters) of the structure:

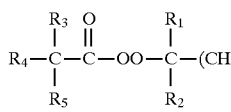 —(CH$_2$)$_l$—(C≡C)$_m$—(CH$_2$)$_n$—(C≡C)$_o$—(CH$_2$)$_p$— 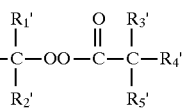

where l, m, n, o and p are 0 to 5 with the proviso that the sum of l, m, n, o and p is at least 1, $R_1$ and $R_2$ are alkyl radicals of 1 to 7 carbons, phenyl radicals or concatenate to form, along with the C atom to which they are attached, a cyclohexane ring, $R_3$, $R_4$ and $R_5$ are alkyl radicals of 1 to 8 carbons with the proviso that not more than one of the $R_3$, $R_4$ and $R_5$ radicals is a methyl radical, and $R_1'$, $R_2'$, $R_3'$, $R_4'$, and $R_5'$ are each the same as $R_1$, $R_2$, $R_3$, $R_4$ and $R_5$, respectively.

The diperoxyester structures of this art do not anticipate the novel bis(mono- and diperoxyoxalates) of Structure A.

Definitions

The 10 hour half-life temperature of an organic peroxide) is defined as the temperature at which half (50%) of the peroxide decomposes in 10 hours.

t-Cycloalkyl refers to the monoradical structure,

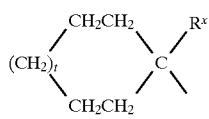

where t is 0 to 2 and $R^x$ is a lower alkyl radical of 1 to 4 carbons, t-alkynyl is the monoradical structure,

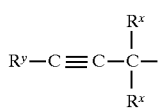

where $R^y$ is hydrogen or a lower alkyl radical of 1 to 4 carbons, and t-aralkyl is the monoradical structure,

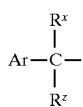

where $R^z$ is the same or different than $R^x$ and is a lower alkyl radical of 1 to 4 carbons, and Ar is an aryl radical of 6 to 10 carbons.

When any generalized functional group or index, such as R, $R^1$, $R^2$, x, n, etc., appears more than once in a general formula or structure, the meaning of each is independent of one another.

SUMMARY OF THE INVENTION

The invention provides in a composition aspect, a novel bis(mono- or diperoxyoxalate) of Structure A:

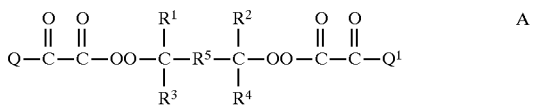

where $R^1$, $R^2$, $R^3$ and $R^4$ are the same or different and are alkyl radicals of 1 to 4 carbons, preferably, alkyl radicals of 1 to 2 carbons, more preferably, methyl radicals, $R^5$ is a diradical selected from —(CH$_2$)n—, where n is 1 to 6, —C≡C—, —C≡C—C≡C—, 1,4-phenylene, substituted or unsubstituted 1,3-phenylene, the substituent being the structure,

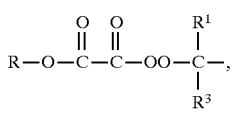

preferably, $R^5$ is a diradical selected from —(CH$_2$)n—, where n is 1 to 2, and —C≡C—, more preferably, $R^5$ is —(CH$_2$)$_2$—, Q and $Q^1$ are independently selected from the group consisting of chloro, bromo, R—O, and $R^6$—OO, where R is selected from the group consisting of H, a substituted or unsubstituted alkyl radical of 1 to 24 carbons, substituents being one or more alkyl radicals of 1 to 6 carbons, alkoxy radicals of 1 to 6 carbons, aryloxy radicals of 6 to 10 carbons, fluoro, chloro, bromo, carboxy and cyano, a substituted or unsubstituted alkenyl radical of 3 to 12 carbons, substituents being one or more lower alkyl radicals of 1 to 4 carbons, a substituted or unsubstituted aryl radical of 6 to 10 carbons, substituents being one or more alkyl radicals of 1 to 6 carbons, alkoxy radicals of 1 to 6 carbons, aryloxy radicals of 6 to 10 carbons, chloro, bromo and cyano, a substituted or unsubstituted aralkyl radical of 7 to 13 carbons, substituents being one or more alkyl radicals of 1 to 6 carbons, a substituted or unsubstituted cycloalkyl radical of 5 to 12 carbons optionally having one or more oxygen or nitrogen atoms in the cycloalkane ring, with substituents being one or more lower alkyl radicals of 1 to 4 carbons, a substituted or unsubstituted bicycloalkyl radical of 6 to 14 carbons, with substituents being one or more lower alkyl radicals of 1 to 4 carbons, a substituted or unsubstituted tricycloalkyl radical of 7 to 16 carbons, with substituents being one or more lower alkyl radicals of 1 to 4 carbons, and, R can. additionally be structure (a),

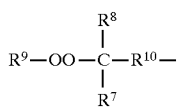

where $R^{10}$ is an unsubstituted alkylene diradical of 1 to 3 carbons or a substituted alkylene diradical of 1 to 3 carbons, substituents being one or more lower alkyl radicals of 1 to 4 carbons, $R^7$ and $R^8$ are alkyl radicals of 1 to 4 carbons, $R^9$ is selected from unsubstituted t-alkyl radicals of 4 to 12 carbons, substituted t-alkyl radicals of 4 to 12 carbons, t-cycloalkyl radicals of 6 to 13 carbons, t-alkynyl radicals of 5 to 9 carbons, t-aralkyl radicals of 9 to 13 carbons, unsubstituted aroyl radicals of 7 to 11 carbons, substituted aroyl radicals of 7 to 11 carbons, where the substituent for the t-alkyl radicals is a t-alkylperoxy radical of 4 to 8 carbons and the substituents for the aroyl radicals are one or more lower alkyl radicals of 1 to 4 carbons, alkoxy radicals of 1 to 4 carbons, phenyl radicals, acyloxy radicals of 2 to 8 carbons, t-alkylperoxycarbonyl radicals of 5 to 9 carbons, fluoro, chloro or bromo, and $R^9$ can also be structures (b), (c) and (d)

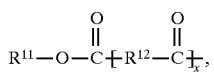

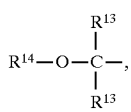

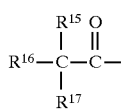

where x is 0 or 1, $R^{11}$ is a substituted or unsubstituted alkyl radical of 1 to 18 carbons, substituents being one or more alkyl radicals of 1 to 6 carbons, t-alkylperoxy radicals of 4 to 8 carbons, alkoxy radicals of 1 to 6 carbons, aryloxy radicals of 6 to 10 carbons, hydroxy, chloro, bromo or cyano or a substituted or unsubstituted cycloalkyl radical of 5 to 12 carbons optionally having one or more oxygen or nitrogen atoms in the cycloalkane ring, with substituents being one or more lower alkyl radicals of 1 to 4 carbons, and, $R^{12}$ is selected from a substituted or unsubstituted alkylene diradical of 2 to 3 carbons, substituents being one or more lower alkyl radicals of 1 to 4 carbons, or a substituted or unsubstituted 1,2-, 1,3- or 1,4-phenylene diradical, substituents being one or more lower alkyl radicals of 1 to 4 carbons, chloro, bromo, nitro or carboxy, and, $R^{13}$ is a lower alkyl radical of 1 to 4 carbons, and, additionally, the two $R^{13}$ radicals may be concatenated to form an alkylene diradical of 4 to 5 carbons, $R^{14}$ is a lower alkyl radical of 1 to 4 carbons, $R^{15}$, $R^{16}$ and $R^{17}$ are selected from hydrogens, alkyl radicals of 1 to 8 carbons, aryl radicals of 6 to 10 carbons, alkoxy radicals of 1 to 8 carbons and aryloxy radicals of 6 to 10 carbons, preferably, R selected from the group consisting of H, a substituted or unsubstituted alkyl radical of 1 to 22 carbons, substituents being one or more alkyl radicals of 1 to 6 carbons, alkoxy radicals of 1 to 6 carbons, aryloxy radicals of 6 to 10 carbons, fluoro, chloro, bromo, carboxy and cyano, a substituted or unsubstituted aralkyl radical of 7 to 13 carbons, substituents being one or more alkyl radicals of 1 to 6 carbons, a substituted or unsubstituted cycloalkyl radical of 5 to 12 carbons, substituents being one or more lower alkyl radicals of 1 to 4 carbons, a substituted or unsubstituted bicycloalkyl radical of 6 to 14 carbons, with substituents being one or more lower alkyl radicals of 1 to 4 carbons, a substituted or unsubstituted tricycloalkyl radical of 7 to 16 carbons, with substituents being one or more lower alkyl radicals of 1 to 4 carbons, and structure (a), more preferably, R is selected from the group consisting of H, a substituted or unsubstituted alkyl radical of 1 to 22 carbons, substituents being one or more alkyl radicals of 1 to 6 carbons, alkoxy radicals of 1 to 6 carbons, aryloxy radicals of 6 to 10 carbons, chloro, bromo, carboxy and cyano, a substituted or unsubstituted cycloalkyl radical of 5 to 12 carbons, substituents being one or more lower alkyl radicals of 1 to 4 carbons, a substituted or unsubstituted bicycloalkyl radical of 6 to 14 carbons, with substituents being one or more lower alkyl radicals of 1 to 4 carbons, and structure (a), and, $R^6$ is selected from an unsubstituted t-alkyl radical of 4 to 12 carbons, a substituted t-alkyl radical of 4 to 12 carbons, a t-cycloalkyl radical of 6 to 13 carbons, a t-alkynyl radical of 5 to 9 carbons, and a t-aralkyl radical of 9 to 13 carbons, where the substituent for the t-alkyl radical is a t-alkylperoxy radical of 4 to 8 carbons, preferably, Q and $Q^1$ are the same or different and are selected from the group consisting of chloro, bromo, and R—O, more preferably, Q and $Q^1$ are the same and are selected from the group consisting of chloro and R—O.

The invention provides in a process aspect a process for the initiation of free radical addition of olefinically unsaturated substrates selected from:

Novel processes using a peroxide composition of Structure A as a curing agent for the curing of unsaturated polyester resin compositions by heating such resins in the presence of initiating amounts of the peroxide composition of Structure A at appropriate temperatures, and, Novel processes using a peroxide composition of Structure A as a free-radical initiator for polymerizing ethylenically unsaturated monomers [such as styrene, ethylene, vinyl chloride, allyl diglycol carbonate (ADC), etc.] by the use of initiating amounts of the peroxide composition of Structure A at appropriate temperatures.

DETAILED DESCRIPTION

Novel Bis(mono- and diperoxyoxalate) Compositions of Structure A

Preparative Methods

The novel bis(mono- and diperoxyoxalate) compositions of Structure A can be prepared by reacting dihydroperoxides of Structure B,

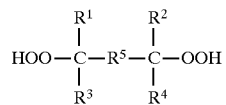

with oxalyl halides, alkyl halooxalates or t-alkylperoxy halooxalates of Structure C,

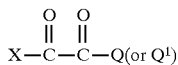

[where X=Br or Cl; Q (or $Q^1$)=Br, Cl, R—O, or $R^6$—OO] C at −90° C. to 50° C., optionally in the presence of an inorganic or organic base, and optionally in the presence one or more solvents. The compositions of Structure C are oxalyl halides, e.g., oxalyl bromide and oxalyl chloride, when X and Q are Br and Cl. The compositions of Structure C are alkyl halooxalates when X is Br or Cl and Q is R—O. The compositions of Structure C are t-alkylperoxy halooxalates when X is Br or Cl and Q is $R^6$—OO.

Non-limiting examples of suitable optional solvents include pentane, hexanes, heptanes, dodecanes, odorless mineral spirits mixtures, toluene, xylenes, cumene, methylene chloride, ethyl acetate, 2-ethylhexyl acetate, isobutyl isobutyrate, dimethyl adipate, dimethyl succinate, dimethyl glutarate (or mixtures thereof), dimethyl phthalate, dibutyl phthalate, benzyl butyl phthalate, diethyl ether, methyl t-butyl ether, 2-methoxyethyl acetate and others.

Non-limiting examples of suitable optional bases include triethylamine, tributylamine, N,N-diisopropylethylamine, 2,2,6,6-tetramethylpiperidine, N,N-dimethylaniline, N,N-dimethylaminopyridine, 2,4,6-colidine, urea, tetramethylurea, sodium hydroxide, sodium carbonate, sodium hydrogen carbonate, potassium hydroxide, potassium carbonate, potassium hydrogen carbonate, calcium hydroxide, magnesium hydroxide, barium hydroxide, calcium carbonate and trisodium phosphate.

Non-limiting examples of suitable dihydroperoxides of Structure B that can be reacted with compositions of Structure C include 2,5-dimethyl-2,5-dihydroperoxyhexane, 2,5-dimethyl-2,5-dihydroperoxy-3-hexyne, 3,6-dimethyl-3,6-3, 6-dimethyl-3,6-dihydroperoxy-4-octyne, 2,7-dimethyl-2,7-dihydroperoxyoctane, 2,7-dimethyl-2,7-dihydroperoxy-3,5-octadiyne, 1,3-diisopropylbenzene dihydroperoxide, 1,4-diisopropylbenzene dihydroperoxide and 1,3,5-triisopropylbenzene trihydroperoxide.

Non-limiting examples of suitable oxalyl halides include oxalyl bromide and oxalyl chloride. Non-limiting examples of suitable alkyl halooxalates of Structure C (X=Br or Cl; Q=R—O) that can be reacted with dihydroperoxides of Structure B include methyl chlorooxalate (also known as methyl oxalyl chloride and methyl chloroglyoxylate), ethyl bromooxalate, ethyl chlorooxalate, isopropyl chlorooxalate, n-butyl chlorooxalate, t-butyl chlorooxalate, 2-ethylhexyl chlorooxalate, dodecyl chlorooxalate, hexadecyl chlorooxalate, docosyl chlorooxalate, 2,2,2-trifluoroethyl chlorooxalate, allyl chlorooxalate, phenyl chlorooxalate, 2-phenoxyethyl chlorooxalate, cyclohexyl chlorooxalate, 4-t-butylcyclohexyl chlorooxalate, menthyl chlorooxalate, bornyl chlorooxalate, isobornyl chlorooxalate, exo-norbornyl chlorooxalate, endonorbornyl chlorooxalate, 1-adamantyl chlorooxalate, 2-adamantyl chlorooxalate, benzyl chlorooxalate, 3-t-butylperoxy-1,3-dimethylbutyl chlorooxalate and 3-(2-ethylhexanoylperoxy)-1,3-dimethylbutyl chlorooxalate. The above alkyl halooxalates can be prepared by reacting 0% to 100% excess oxalyl bromide or oxalyl chloride with the corresponding alkanol until the reaction is completed. The excess oxalyl halide can be removed by stripping or by distillation. Non-limiting examples of suitable alkanols that can be reacted with oxalyl halides to form alkyl halooxalates of Structure C include methanol, ethanol, isopropanol, t-butanol, n-butanol, 2-ethylhexanol, dodecanol, hexadecanol, docosanol, hexafluoroamyl alcohol, 2,2,2-trifluoroethanol, allyl alcohol, cyclohexanol, 4-t-butylcyclohexanol, menthol, exo-norborneol, endonorborneol, borneol, isoborneol, 1-adamantanol, 2-adamantanol, phenol, 2-phenoxyethanol, benzyl alcohol, 3-t-butylperoxy-1,3-dimethylbutanol and 3-hydroxy-1,1-dimethylbutyl 2-ethylperoxyhexanoate.

The t-alkylperoxy halooxalates of Structure C (X=Br or Cl; Q=$R^6$—OO) can be prepared by reacting excess oxalyl halides, e.g., oxalyl bromide and oxalyl chloride, with t-alkyl hydroperoxides, optionally in the presence one or more solvents. The excess oxalyl halide and optional solvents can be removed from the t-alkylperoxy halooxalates by stripping or by distillation. Non-limiting examples of suitable optional solvents are given above. Non-limiting examples of suitable t-alkyl hydroperoxides for preparing the t-alkylperoxy halooxalates of Structure C include t-butyl hydroperoxide, t-amyl hydroperoxide, t-hexyl hydroperoxide, 1,1,3,3-tetramethylbutyl hydroperoxide, 1-methylcyclohexyl hydroperoxide, paramenthane hydroperoxide, 2-hydroperoxy-2-methyl-3-butyne, α-cumyl hydroperoxide, and diisopropylbenzene monohydroperoxide. Non-limiting examples of suitable t-alkylperoxy halooxalates of Structure C include t-butylperoxy chlorooxalate, t-amylperoxy chlorooxalate, 1,1,3,3-tetramethylbutylperoxy chlorooxalate, and isopropyl-α-cumylperoxy chlorooxalate.

An alternate two-step synthetic route to the compositions of Structure A where Q and $Q^1$ are R—O involves the initial reaction of dihydroperoxide of Structure B with excess oxalyl halides followed by removal of excess oxalyl halide to form the novel compositions of Structure D,

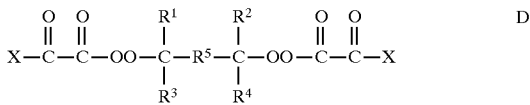

and subsequent reaction of the compositions of Structure D with water or an alkanol in the presence of a suitable inorganic or organic base, and optionally in the presence one or more solvents.

Non-limiting examples of suitable dihydroperoxides of Structure B, inorganic or organic bases, optional solvents, and alkanols are given above. Suitable novel compositions of Structure D include 2,5-dimethyl-2,5-di(chlorocarbonylcarbonylperoxy)hexane, 2,5-dimethyl-2,5-di(chlorocarbonylcarbonylperoxy)-3-hexyne, 3,6-dimethyl-3,6-di(chlorocarbonylcarbonylperoxy)octane, 3,6-dimethyl-3,6-di(chlorocarbonylcarbonylperoxy)-4-octyne, 2,7-dimethyl-2,7-di(chlorocarbonylcarbonylperoxy)octane, 2,7-dimethyl-2,7-di(chlorocarbonylcarbonylperoxy)-3,5-octadiyne, and 1,3-di(2-chlorocarbonylcarbonylperoxy-2-propyl)benzene.

An alternate two-step synthetic route to the compositions of Structure A where Q and $Q^1$ are $R^6$—OO involves the initial formation of the novel compositions of Structure D and subsequent reaction of the compositions of Structure D with t-alkyl hydroperoxides in the presence of a suitable inorganic or organic base, and optionally in the presence one or more solvents.

Non-limiting examples of suitable novel compositions of Structure D, inorganic or organic bases, optional solvents, and t-alkyl hydroperoxides are given above.

Novel Bis(mono- and diperoxyoxalate)
Compositions of Structure A

Illustrative Examples

Non-limiting examples of the novel bis(mono- and diperoxyoxalate) compositions of Structure A, in addition to those in the teaching examples, include the following:

1,4-di(2-chlorocarbonylcarbonylperoxy-2-propyl)benzene, 2,5-dimethyl-2,5-di(carboxycarbonylperoxy)-3-hexyne, 2,5-dimethyl-2,5-di(chlorocarbonylcarbonylperoxy)-3-hexyne, 2,5-dimethyl-2,5-di(methoxycarbonylcarbonylperoxy)hexane, 2,5-dimethyl-2,5-di(methoxycarbonylcarbonylperoxy)-3-hexyne, 3,6-dimethyl-3,6-di(methoxycarbonylcarbonylperoxy)octane, 3,6-dimethyl-3,6-di(methoxycarbonylcarbonylperoxy)-4-octyne, 2,7-dimethyl-2,7-di(methoxycarbonylcarbonylperoxy)octane, 2,7-dimethyl-2,7-di(methoxycarbonylcarbonylperoxy)-3,5-octadiyne [where the methoxycarbonylcarbonylperoxy radical has the structure,

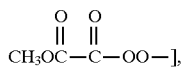

2,5-dimethyl-2,5-di(isopropoxycarbonylcarbonylperoxy) hexane, 2,5-dimethyl-2,5-di(n-butoxycarbonylcarbonylperoxy)hexane, 2,5-dimethyl-2,5-di(dodecyloxycarbonylcarbonylperoxy)hexane, 2,5-dimethyl-2,5-di(hexadecyloxycarbonylcarbonylperoxy)hexane, 2,5-dimethyl-2,5-di(2,2,2-trifluoroethoxycarbonylcarbonylperoxy)hexane, 2,5-dimethyl-2,5-di[(2-phenoxyethoxy)carbonylcarbonylperoxy]hexane, 2,5-dimethyl-2,5-di(alloxycarbonylcarbonylperoxy)hexane, 2,5-dimethyl-2,5-di(cyclohexoxycarbonylcarbonylperoxy) hexane, 2,5-dimethyl-2,5-di[(4-t-butylcyclohexoxy) carbonylcarbonylperoxy]-3-hexyne, 2,5-dimethyl-2,5-di(menthyloxycarbonylcarbonylperoxy)hexane, 2,5-dimethyl-2,5-di[(exo-norbornyloxy)carbonylcarbonylperoxy]hexane, 2,5-dimethyl-2,5-di[(1-adamantoxy)carbonylcarbonylperoxy]hexane, 2,5-dimethyl-2,5-di[(2-adamantoxy)carbonylcarbonylperoxy]hexane, 2,5-dimethyl-2,5-di(phenoxycarbonylcarbonylperoxy)hexane, 2,7-dimethyl-2,7-di(benzyloxycarbonylcarbonylperoxy) octane, 2,5-dimethyl-2,5-di(benzyloxycarbonylcarbonylperoxy)-3-hexyne, 2,5-dimethyl-2,5-di[(3-t-butylpercxy-3-methylbutoxy)carbonylcarbonylperoxy]hexane, 2,5-dimethyl-2,5-di[{3-(2-ethylhexanoylperoxy)-1,3-dimethylbutoxy}carbonylcarbonylperoxy]hexane, 2,7-dimethyl-2,7-di(bornyloxycarbonylcarbonylperoxy)octane, 1,3-di[1-methyl-i-(dodecyloxycarbonylcarbonylperoxy)-ethyl]benzene, 1,4-di[1-methyl-1-(hexoxycarbonylcarbonylperoxy)ethyl]benzene, 1,3,5-tri[1-methyl-i-(decyloxycarbonylcarbonylperoxy)ethyl]benzene, 2,5-dimethyl-2,5-di(t-butylperoxycarbonylcarbonylperoxy)-3-hexyne, and 2,5-dimethyl-2,5-di(t-amylperoxycarbonylcarbonylperoxy) hexane.

Novel Bis(mono- and diperoxyoxalate)
Compositions of Structure A - Utility

A. Polymerization of Ethylenically Unsaturated Monomers

In the free-radical polymerizations of ethylenically unsaturated monomers at suitable temperatures and pressures the novel peroxide compositions of Structure A of this invention were found to be effective initiators with respect to efficiency (reduced initiator requirements, etc.). Ethylenically unsaturated monomers include olefins, such as ethylene, propylene, styrene, alpha-methylstyrene, p-methylstyrene, chlorcstyrenes, bromostyrenes, vinylbenzyl chloride, vinylpyridine and divinylbenzene; diolefins, such as 1,3-butadiene, isoprene and chloroprene; vinyl esters, such as vinyl acetate, vinyl propionate, vinyl laurate, vinyl benzoate and divinyl carbonate; unsaturated nitriles, such as acrylonitrile and methacrylonitrile; acrylic acid and methacrylic acid and their anhydrides, esters and amides, such as acrylic acid anhydride, allyl, methyl, ethyl, n-butyl, 2-hydroxyethyl, glycidyl, lauryl and 2-ethylhexyl acrylates and methacrylates, and acrylamide and methacrylamide; maleic anhydride and itaconic anhydride; maleic, itaconic and fumaric acids and their esters; vinyl halo and vinylidene dihalo compounds, such as vinyl chloride, vinyl bromide, vinyl fluoride, vinylidene chloride and vinylidene fluoride; perhalo olefins, such as tetrafluoroethylene, hexafluoropropylene and chlorotrifluoroethylene; vinyl ethers, such as methyl vinyl ether, ethyl vinyl ether and n-butyl vinyl ether; allyl esters, such as allyl acetate, allyl benzoate, allyl ethyl carbonate, triallyl phosphate, diallyl phthalate, diallyl fumarate, diallyl glutarate, diallyl adipate, diallyl carbonate diethylene glycol bis(allyl carbonate) (i.e., ADC); acrolein; methyl vinyl ketone; or mixtures thereof.

Temperatures of 0° C. to 100° C., preferably 20° C. to 90° C., more preferably 30° C. to 75° C. and levels of bis(mono- and diperoxyoxalates) of Structure A (on a pure basis) of 0.002 to 10% or more, preferably 0.005% to 2%, more preferably 0.01% to 1% by weight based on monomer, are normally employed in conventional polymerizations and copolymerizations of ethylenically unsaturated monomers. The novel peroxide compositions of this invention can be used in combination with other free-radical initiators such as those disclosed at the bottom of column 4 and the top of column 5 of U.S. Pat. No. 4,525,308 (Jun. 25, 1985, to Pennwalt Corporation). Using the peroxide compositions of this invention in combination with these initiators adds flexibility to the processes of polymer producers and allow them to "fine tune" their polymerization processes.

B. Curing of Unsaturated Polyester Resins

In the curing of unsaturated polyester resin compositions by heating at suitable curing temperatures in the presence of free-radical. curing agents, the novel bis(mono- and diperoxyoxalate) compositions of Structure A of this invention exhibit enhanced curing activity in the curable unsaturated polyester resin compositions. Unsaturated polyester resins that can be cured by the novel bis(mono- and diperoxyoxalate) compositions of this invention usually include an unsaturated polyester and one or more ethylenically unsaturated monomers.

The unsaturated polyesters are, for instance, polyesters as they are obtained by esterifying at least one ethylenically unsaturated di- or polycarboxylic acid, anhydride or acid halide, such as maleic acid, fumaric acid, glutaconic acid, itaconic acid, mesaconic acid, citraconic acid, allylmalonic acid, tetrahydrophthalic acid, and others, with saturated and unsaturated di- or polyols, such as ethylene glycol, diethylene glycol, triethylene glycol, 1,2- and 1,3-propanediols, 1,2-, 1,3- and 1,4-butanediols, 2,2-dimethyl-1,3-propanediol, 2-hydroxymethyl-2-methyl-1,3-propanediol, 2-buten-1,4-diol, 2-butyn-1,4-diol, 2,4,4-trimethyl-1,3-pentanediol, glycerol, penta-erythritol, mannitol and others. Mixtures of such di- or polyacids and/or mixtures of such di- or polyols may also be used. The di- or polycarboxylic acids may be partially replaced by saturated di- or polycarboxylic acids, such as adipic acid, succinic acid, sebacic acid and other, and/or by aromatic di- or polycarboxylic acids, such as phthalic acid, trimellitic acid, pyromellitic acid, isophthalic acid and terephthalic acid. The acids used may be substituted by groups such as halogen. Examples of such suitable halogenated acids are, for instance, tetrachlorophthalic acid, tetrabromophthalic acid, 5,6-dicarboxy-1,2, 3,4,7,7-hexachlorobicyclo(2.2.1)-2-heptene and others.

The other component of the unsaturated polyester resin composition, the polymerizable monomer or monomers, can preferably be ethylenically unsaturated monomers, such as styrene, alpha-methylstyrene, p-methylstyrene, chlorostyrenes, bromostyrenes, vinylbenzyl chloride, divinylbenzene, diallyl maleate, dibutyl fumarate, triallyl phosphate, triallyl cyanurate, diallyl phthalate, diallyl fumarate, methyl acrylate, methyl methacrylate, n-butyl acrylate, n-butyl methacrylate, ethyl acrylate, and others, or mixtures thereof, which are copolymerizable with said unsaturated polyesters.

A preferred unsaturated polyester resin composition contains as the unsaturated polyester component the esterification product of 1,2-propanediol (a polyol), maleic anhydride (an anhydride of an unsaturated polycarboxylic acid) and phthalic anhydride (an anhydride of an aromaltic dicarboxylic acid) as well as the monomer component, styrene.

Other types of unsaturated polyester resin compositions can be cured using the novel peroxide compositions of this invention as curing catalysts. These resins, called unsaturated vinyl ester resins, consist of a vinyl ester resin portion and one or more polymerizable monomer components. The vinyl ester resin component can be made by reacting a chloroepoxide, such as epichlorohydrin, with. appropriate amounts of a bisphenol such as Bisphenol A [2,2-(4-hydroxyphenyl)propane], in the presence of a base, such as sodium hydroxide, to yield a condensation product having terminal epoxy groups derived from the chloroepoxide. Subsequent reaction of the condensation product with polymerizable unsaturated carboxylic acids, such as acrylic acid and methacrylic acid, in the presence or absence of acidic or basic catalysts, results in formation of the vinyl ester resin component. Normally, styrene is added as the polymerizable monomer component to complete the preparation of the unsaturated vinyl ester resin composition.

Temperatures of about 20° C. to 200° C. and levels of novel bis(mono- and diperoxyoxalates) of Structure A of about 0.05% to 5% or more, preferably 0.10% to 4%, more preferably 0.25% to 36% by weight of curable unsaturated polyester resin composition are normally employed.

The unsaturated polyester resin compositions described above can be filled with various materials, such as sulfur, glass, carbon and boron fibers, carbon blacks, silicas, metal silicates, clays, metal carbonates, antioxidants (AO's), heat, ultraviolet (UV) and light stabilizers, sensitizers, dyes, pigments, accelerators, metal oxides, such as zinc oxide, blowing agents, nucleating agents and others.

C. Curing of Allyl Diglycol Carbonate (ADC) Resins

In the curing or polymerizing of diethylene glycol bis (allyl carbonate) (ADC),

by heating ADC monomer at suitable curing temperatures in the presence of free-radical curing agents, the novel bis (mono- and diperoxyoxalate) compositions of Structure A of this invention exhibit enhanced curing or polymerizing activity for ADC monomer compositions. ADC was introduced commercially as CR-39 monomer (CAS Reg. No. 142-22-3) by Pittsburgh Plate Glass Company (PPG) and is produced by reacting diethylene glycol bis(chloroformate) with allyl alcohol in the presence of alkali (R. Dowbenko, in J. I. Kroschwitz and M. Howe-Grant, eds., Kirk-Othimer—Encyclopedia of Chemical Technology, "Allyl Monomers and Polymers," Fourth Edition, Vol. 2, Wiley-Interscience Publication, John Wiley & Sons, Inc., New York, 1992, pp 163–168). The ADC monomer can be cured or polymerized alone or with other co-monomers such as such as acrylic acid esters, methacrylic acid esters, allyl esters, diallyl dicarboxylates (e.g., diallyl phthalate), maleic anhydride and other monomers to produce clear castings or lenses that are transparent, tough, break-resistant and solvent-resistant. Curing or polymerizing of ADC monomer compositions are carried out in bulk (no solvent present). In general, curing or polymerizing of ADC monomer compositions to form cast sheets or lenses is carried out in two stages. The first stage involves the major part of the polymerization and occurs in the presence of the curing initiator, usually a lower dialkyl peroxydicarbonate, at temperatures of 35° C. to 120° C. Curing or polymerization times vary from about 5 hours to 50 hours. Generally a time-temperature profile is employed in the first stage. An example of a time-temperature profile is given below:

| TYPICAL CURE TEMPERATURE SCHEDULE FOR CURING OF ADC | |
|---|---|
| TIME (HOURS) | TEMPERATURE (°C.) |
| 0.0 | 61 |
| 1.0 | 62 |
| 3.0 | 64 |
| 7.0 | 68 |
| 8.0 | 69 |
| 8.5 | 74 |
| 9.0 | 79 |
| 9.5 | 86.5 |
| 10.0 | 96.5 |
| 10.5 | 115 |
| 10.75 | 85 |
| 11.0 | 60 |
| 11.25 | 40 |
| 11.5 | 30 |

The second stage of the curing or polymerizing of ADC monomer compositions involves post-curing or annealing of the ADC resin for one to several hours at 100° C. to 150° C. An example of post-curing of the ADC resin would be 2 hours at 115° C.

Levels of the novel bis(mono- and diperoxyoxalate) compositions of about 1% to 6% or more, preferably 2% to 5%, more preferably 2.5% to 4% by weight of curable or polymerizable ADC monomer composition, are normally employed.

The ADC resin compositions described above can be filled with various materials, such as antioxidants (AO's), heat, ultraviolet (UV) and light stabilizers, tints, photochromic additives and dyes. In addition, the ADC resin compositions can contain additives such as acrylic polymers and the anti-shrink, low molecular weight acrylic resins disclosed in U.S. Pat. No. 4,217,433 (Aug. 12, 1980, to Pennwalt Corporation, now Elf Atochem North America, Inc.). Such anti-shrink additives are employed to counter the 14% shrinkage that occurs when ADC monomer is polymerized.

Novel Bis(mono- and diperoxyoxalate)
Compositions of Structure A

PREPARATIVE AND UTILITY EXAMPLES

The following examples further illustrate the best mode contemplated by the inventor for practicing the instant invention, and are presented to provide detailed preparative and utility illustrations of the invention and are not intended to limit the breadth and scope of the invention.

Example 1

Preparation of 2,5-Dimethyl-2,5-di (ethoxycarbonylcarbonylperoxy)hexane (I-1)

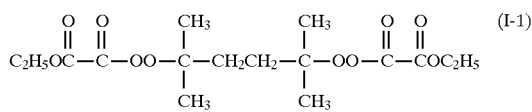

(I-1)

In this example ethyl chlorooxalate was reacted with 2,5-dimethyl-2,5-dihydroperoxyhexane, in the presence of pyridine, to yield the product:

A 500 mL water-jacketed reactor, equipped with a mechanical stirrer, a thermometer and an addition funnel, was charged with 200 mL of methylene chloride, 7.2 g (40.0 mmoles) of 98% 2,5-dimethyl-2,5-dihydroperoxyhexane and 7.0 g (88.0 mmoles) of pyridine. The stirred mixture was cooled to 0° C. and to it was slowly added a solution of 11.8 g (82.0 mmoles) of 98% ethyl chlorooxalate in 40 mL of methylene chloride over a period of 10–15 minutes. A solid, pyridinium chloride, formed shortly after the addition was started. After the addition was completed the reaction mass was stirred for 60 minutes at 0° C. to 10° C. after which 50 mL of water was added and the reaction mass was stirred an additional 10 minutes at 50° C. The upper aqueous layer was then separated and the organic layer was washed with 40 mL of aqueous 5% HCl solution and then twice with 100 mL portions of water. The product solution was dried over 5% by weight of anhydrous $MgSO_4$, and after separation of the spent desiccant by filtration, the solvent was removed in vacuo leaving 12.7 g of colorless liquid (84.1% of theory, uncorrected). An IR spectrum of the product showed a small OH band in the 3500 $cm^{-1}$ region. A major monoperoxyoxalate carbonyl band was present at 1780 $cm^{-1}$ and a major oxalate carbonyl band was present at about 1735 $cm^{-1}$. The product had a rapid heat test [J. Varjavandi and O. L. Mageli, J. Chem. Ed. 48, A451 (1971)] result of 45° C. which confirmed that the product was an extremely low temperature peroxide. The product contained 7.47% active oxygen (theory, 8.46%) according to a peroxyester active oxygen method, therefore, the assay of the product was 88.36% and the corrected yield was 74.3%.

Based on the method of preparation, yield data (assay and corrected yield), rapid heat test, data and infrared spectral data the product obtained in this reaction was the desired title product.

Example 2

Preparation of 2,5-Dimethyl-2,5-di (docosyloxycarbonylcarbonylperoxy)hexane (I-2)

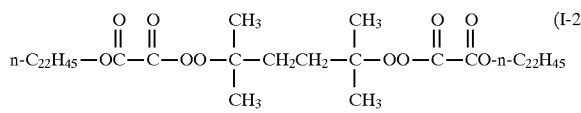

(I-2)

In this example the product was prepared in two synthetic steps. In the first step docosanol was reacted with 50% molar excess of oxalyl chloride. Upon completion of the reaction the excess oxalyl chloride was stripped from the product at reduced pressure to produce docosyl chlorooxalate having an assay of 91.4% and in a corrected yield of 92.5%. In the second step docosyl chlorooxalate was reacted with 2,5-dimethyl-2,5-dihydroperoxyhexane, in the presence of pyridine, to yield the product:

A 500 mL 3-neck reactor, equipped with a magnetic stirring bar, a condenser, a thermometer and an addition funnel, was charged with 60 mL of pentane, 2.0 g (11.0 mmoles) of 98% 2,5-dimethyl-2,5-dihydroperoxyhexane and 2.4 g (30.0 mmoles) of pyridine. The stirred mixture was cooled to 0° C. and to it was slowly added a solution of 10.0 g (22.0 mmoles) of 91.4% docosyl chlorooxalate in 250 mL of pentane over a period of 20 minutes. After the addition was completed the reaction mass was stirred for 90 minutes at 0° C. after which 100 mL of water and 100 mL of hexane were added and the reaction mass was stirred an additional 10 minutes at 5° C. The lower aqueous layer was then separated and the organic layer was washed with aqueous 5% HCl solution and with water until the pH of the spent water washes was 7.0. The product solution was dried over 5% by weight of anhydrous $MgSO_4$, and, after separation of the spent desiccant by filtration, the solvent was removed in vacuo leaving 6.7 g of a white solid (65% of theory, uncorrected) that had a melting point of 71° C. An IR spectrum of the product as a nujol mull showed no OH band in the 3500 $cm^{-1}$ region. A major monoperoxyoxalate carbonyl band was present at 1775 $cm^{-1}$. The product had a rapid heat test result of 72° C. which confirmed that the product was a very low temperature peroxide. The product contained 3.21% active oxygen (theory, 3.41%) according to a peroxyester active oxygen method, therefore, the assay of the product was 94.1% and the corrected yield was 61.2%.

Based on the method of preparation, yield data, rapid heat test data and infrared spectral data the product obtained in this reaction was the desired title product.

Example 3

Preparation of 2,5-Dimethyl-2,5- [di(4-t-butyl-cyclohexoxy)carbonylcarbonylperoxy]hexane (I-3)

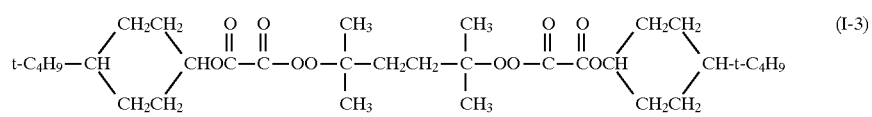

(I-3)

In this example the product was prepared in two synthetic steps. In the first step 4-t-butylcyclohexanol was reacted with 50% molar excess of oxalyl chloride. Upon completion of the reaction the excess oxalyl chloride was stripped from the product at reduced pressure to produce 4-t-butylcyclohexyl chlorooxalate having an assay of 96.9% and in a corrected yield of 95.3%. In the second step 4-t-butylcyclohexyl chlorooxalate was reacted with 2,5-dimethyl-2,5-dihydroperoxyhexane, in the presence of pyridine, to yield the product:

A 500 mL water-jacketed reactor, equipped with a mechanical stirrer, a thermometer and an addition funnel, was charged with 75 mL of methylene chloride, 3.6 g (20.0 mmoles) of 98% 2,5-dimethyl-2,5-dihydroperoxyhexane and 3.5 g (44.0 mmoles) of pyridine. The stirred mixture was cooled to 0° C. and to it was slowly added a solution of 9.9 g (40.0 mmoles) of 96.9% 4-t-butylcyclohexyl chlorooxalate in 25 mL of methylene chloride over a period of 10–15 minutes. After the addition was completed the reaction mass was stirred for 60 minutes at 0° C. to 10° C. after which 50 mL of water was added and the reaction mass was stirred an additional 10 minutes at 5° C. The upper aqueous layer was then separated and the organic layer was washed with 20 mL of aqueous 5% HCl solution and then twice with 50 mL portions of water. The product solution was dried over 5% by weight of anhydrous $MgSO_4$, and, after separation of the spent desiccant by filtration, the solvent was removed in vacuo leaving 13.7 g of colorless liquid (>100% of theory, uncorrected). An IR spectrum of the product showed a major monoperoxyoxalate carbonyl band at 1790 cm$^{-1}$ and a major oxalate carbonyl band at about 1750 cm$^{-1}$. The product had a rapid heat test result of 57° C. which confirmed that the product was a very low temperature peroxide. The product contained 3.88% active oxygen (theory, 5.34%) according to a peroxyester active oxygen method, therefore, the assay of the product was 72.7% and the corrected yield was 83.0%.

Based on the method of preparation, yield data, rapid heat test data and infrared spectral data the product obtained in this reaction was the desired title product.

Example 4

Preparation of 2,5-Dimethyl-2,5-di (isobornyloxycarbonylcarbonylperoxy)hexane (I-4)

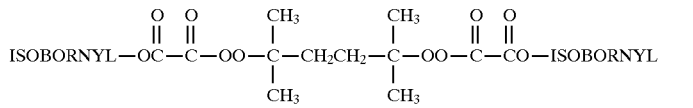

In this example the product was prepared in two synthetic steps. In the first step isoborneol was reacted with 50% molar excess of oxalyl chloride. Upon completion of the reaction the excess oxalyl chloride was stripped from the product at reduced pressure to produce isobornyl chlorooxalate having an assay of 95.2% and in a corrected yield of 91.3%. In the second step isobornyl chlorooxalate was reacted with 2,5-dimethyl-2,5-dihydroperoxyhexane, in the presence of pyridine, to yield the product as described below:

A 500 mL water-jacketed reactor, equipped with a mechanical stirrer, a thermometer and an addition funnel, was charged with 100 mL of methylene chloride, 3.6 g (20.0 mmoles) of 98% 2,5-dimethyl-2,5-dihydroperoxyhexane and 3.5 g (44.0 mmoles) of pyridine. The stirred mixture was cooled to 0° C. and to it was slowly added a solution of 10.3 g (40.0 mmoles) of 95.2% isobornyl chlorooxalate in 20 mL of methylene chloride over a period of 10–15 minutes. A solid, pyridinium chloride, formed shortly after the addition commenced. After the addition was completed the reaction mass was stirred for 60 minutes at 0° C. to 10° C. after which 50 mL of water was added and the reaction mass was stirred an additional 10 minutes at 5° C. The aqueous layer was then separated and the organic layer was washed with 20 mL of aqueous 5% HCl solution and then twice with 50 mL portions of water. The product solution was dried over 5% by weight of anhydrous $MgSO_4$, and, after separation of the spent desiccant by filtration, the solvent was removed in vacuo leaving about 20 g of a viscous, colorless liquid. To this product was added 50 mL of pentane which resulted in precipitation of a solid product. The mixture was cooled to −20° C. and the solid was separated by filtration and air-dried. Obtained was 7.2 g of white solid (60.5% of theory, uncorrected) that had a melting point of 78°–80° C. An IR spectrum of the product as a nujol mull showed no significant OH band in the 3500 cm$^{-1}$ region and a major monoperoxyoxalate carbonyl band was present at 1785 cm$^{-1}$ and a major oxalate carbonyl band was present at about 1735 cm$^{-1}$. The product had a rapid heat test result of 63° C. which confirmed that the product was a very low temperature peroxide. The product contained 5.08% active oxygen (theory, 5.38%) according to a peroxyester active oxygen method, therefore, the assay of the product was 94.4% and the corrected yield was 57.1%.

Based on the method of preparation, yield data, rapid heat test data and infrared spectral data the product obtained in this reaction was the desired title product. 2,5-Dimethyl-2,5-di(isobornyloxycarbonylcarbonylperoxy)hexane (I-4) was found to have a 10 hour half-life temperature of 20° C. in trichloroethylene, therefore, I-4 was an extremely active peroxide compared to the OO-t-alkyl O-alkyl monoperoxyoxalates of the art.

Example 5

Preparation of 2,5-Dimethyl-2,5-di (neopentyloxycarbonylcarbonylperoxy)hexane (I-5)

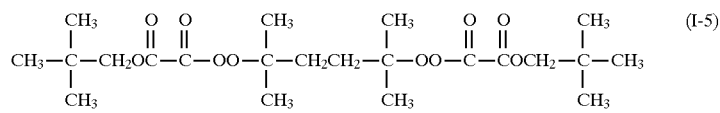

In this example the product was prepared in two synthetic steps. In the first step neopentyl alcohol was reacted with 50% molar excess of oxalyl chloride. Upon completion of the reaction the excess oxalyl chloride was stripped from the product at reduced pressure to produce neopentyl chlorooxalate having an assay of 100% and in a corrected yield of 92.7%. In the second step neopentyl chlorooxalate was reacted with 2,5-dimethyl-2,5-dihydroperoxyhexane, in the presence of pyridine, to yield the product as described below:

A 250 mL 3-neck flask, equipped with a magnetic stirring, a condenser, a thermometer and an addition funnel, and cooled with an ice-water bath, was charged with 60 mL of MTBE, 3.6 g (20.0 mmoles) of 98% 2,5-dimethyl-2,5-dihydroperoxyhexane and 4.5 g (57.0 mmoles) of pyridine. The stirred mixture was cooled to 0° C. and to it was slowly added a solution of 7.5 g (42.0 mmoles) of 100% neopentyl chlorooxalate in 10 mL of MTBE over a period of 10–15 minutes. A solid, pyridinium chloride, formed shortly after the addition commenced. After the addition was completed the reaction mass was stirred for 60 minutes at 2° C. after which 10 mL of water was added and the reaction mass was stirred an additional 10 minutes at 3°–4° C. The aqueous layer was then separated and the organic layer was washed three times with 35 mL of aqueous 5% HCl solution and then twice with 75 mL portions of water. The product solution was dried over 5% by weight of anhydrous MgSO$_4$, and, after separation of the spent desiccant by filtration, the solvent was removed in vacuo leaving 9.1 g of white solid (97.8% of theory, uncorrected) that had a melting point of 35°–37° C. An IR spectrum of the product as a nujol mull showed no significant OH band in the 3500 cm$^{-1}$ region. A major monoperoxyoxalate carbonyl band was present at 1790 cm$^{-1}$ and a major oxalate carbonyl band was present at about 1740 cm$^{-1}$. The product had a rapid heat test result of 54° C. which confirmed that the product was a very low temperature peroxide. The product contained 6.66% active oxygen (theory, 6.92%) according to a peroxyester active oxygen method, therefore, the assay of the product was 96.2% and the corrected yield was 94.2%.

Based on the method of preparation, yield data, rapid heat test data and infrared spectral data the product obtained in this reaction was the desired title product.

Example 6

Preparation of 2,5-Dimethyl-2,5-di (neopentyloxycarbonylcarbonylperoxy)-3-hexyne (I-6)

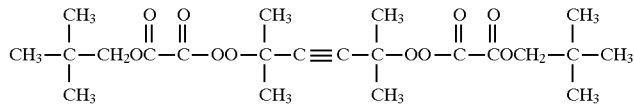

In this example the product was prepared by initially drying a solution of wet, 78% 2,5-dimethyl-2,5-dihydroperoxy-3-hexyne in MTBE with anhydrous MgSO$_4$ and separation of the spent desiccant by filtration, then reaction of the dry 2,5-dimethyl-2,5-dihydroperoxy-3-hexyne solution with neopentyl chlorooxalate in the presence of pyridine, as described below:

A solution of 4.5 g (0.020 mole) of wet 78% 2,5-dimethyl-2,5-dihydroperoxy-3-hexyne in 60 mL of MTBE was dried over 5% by weight of anhydrous MgSO$_4$. After filtering the solution and washing the spent MgSO$_4$ on the filter with three 10 mL portions of fresh MTBE, the combined MTBE solution was then charged into a 250 mL 3-necked flask equipped with a magnetic stirring bar, a condenser, a thermometer and an addition funnel and cooled with an ice-water bath. Then 4.5 g (0.057 mole) of dry pyridine was added. The flask contents were cooled to 0° C. Then to the resulting vigorously stirred solution at about 0° C. was slowly added a solution of 7.5 g (0.042 mole) of 100% neopentyl chlorooxalate in 10 mL of MTBE. A solid pyridinium chloride formed after the addition was started. After the addition was completed, the reaction mass was stirred for 60 minutes at 2° C. after which 10 mL of water was added and the reaction mass was stirred an additional 10 minutes at 3°–4° C. The aqueous layer was then separated and the organic layer washed three times with 35 mL portions of aqueous 5% HCl solution and then twice with 75 mL portions of water. The product solution was dried over 5% by weight of anhydrous MgSO$_4$, and, after separation of the spent desiccant by filtration, the solvent was removed in vacuo leaving 10.0 g of a liquid (>100% of theory, uncorrected). An IR spectrum of the product showed a small OH band in the 3500 cm$^{-1}$ region, a major monoperoxyoxalate carbonyl band at about 1800 cm$^{-1}$ and a major oxalate carbonyl band at about 1750 cm$^{-1}$. The product had a rapid heat test result of 54° C. which confirmed that the product was a very low temperature peroxide. The product contained 6.39% active oxygen (theory, 6.98%) according to a peroxyester active oxygen method, therefore, the assay of the product was 91.5% and the corrected yield was 99.5%.

Based on the method of preparation, yield data, rapid heat test data and infrared spectral data the product obtained in this reaction was the desired title product.

Example 7

Preparation of 2,5-Dimethyl-2,5-di (bornyloxycarbonylcarbonylperoxy)hexane (I-7)

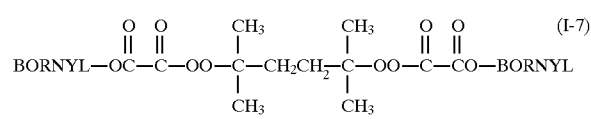

In this example the product was prepared by reacting 98% 2,5-dimethyl-2,5-dihydroperoxyhexane in MTBE with 96.6% bornyl chlorooxalate in the presence of pyridine. The bornyl chlorooxalate was prepared by reacting excess oxalyl chloride with borneol. followed by removal of HCl and excess oxalyl chloride. The procedure is described below:

A 250 mL 3-neck flask, equipped with a magnetic stirring, a condenser, a thermometer and an addition funnel, and cooled with an ice-water bath, was charged with 60 mL of MTBE, 3.6 g (20.0 mmoles) of 98% 2,5-dimethyl-2,5-dihydroperoxyhexane and 4.5 g (57.0 mmoles) of pyridine. The stirred mixture was cooled to 0° C. and to it was slowly added a solution of 10.6 g (42.0 mmoles) of 96.6% bornyl chlorooxalate in 10 mL of MTBE over a period of 10–15 minutes. A solid, pyridinium chloride, formed shortly after the addition commenced. After the addition was completed the reaction mass was stirred for 60 minutes at 2° C. after which 10 mL of water was added and the reaction mass was stirred an additional 10 minutes at 3°–4° C. The aqueous layer was then separated and the organic layer was washed three times with 35 mL of aqueous 5% HCl solution and then twice with 75 mL portions of water. The product solution was dried over 5% by weight of anhydrous MgSO$_4$, and, after separation of the spent desiccant by filtration, the solvent was removed in vacuo leaving 7.4 g of white solid (62.2% of theory, uncorrected) that had a melting point of 80° C. An IR spectrum of the product as a nujol mull showed no significant OH band in the 3500 cm$^{-1}$ region. A major monoperoxyoxalate carbonyl band was present at 1790 cm$^{-1}$ and a major oxalate carbonyl band was present at about 1745 cm$^{-1}$. The product had a rapid heat test result of 54° C. which confirmed that the product was a very low temperature peroxide. The product contained 5.02% active oxygen (theory, 5.38%) according to a peroxyester active oxygen method, therefore, the assay of the product was 93.3% and the corrected yield was 58.8%.

Based on the method of preparation, yield data, rapid heat test data and infrared spectral data the product obtained in this reaction was the desired title product.

Example 8

Preparation of 2,5-Dimethyl-2,5-di (benzyloxycarbonylcarbonylperoxy)hexane (I-8)

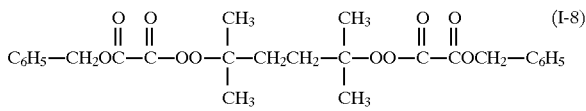

In this example the product was prepared in two synthetic steps. In the first step benzyl alcohol was reacted with 50% molar excess of oxalyl chloride. Upon completion of the reaction the excess oxalyl chloride was stripped from the product at reduced pressure to produce benzyl chlorooxalate having an assay of 96.6% and in a corrected yield of 92.1%. In the second step benzyl chlorooxalate was reacted with 2,5-dimethyl-2,5-dihydroperoxyhexane, in the presence of pyridine, to yield the product as described below:

A 250 mL 3-neck flask, equipped with a magnetic stirring, a condenser, a thermometer and an addition funnel, and cooled with an ice-water bath, was charged with 60 mL of MTBE, 3.6 g (20.0 mmoles) of 98% 2,5-dimethyl-2,5-dihydroperoxyhexane and 4.5 g (57.0 mmoles) of pyridine. The stirred mixture was cooled to 0° C. and to it was slowly added a solution of 8.6 g (42.0 mmoles) of 96.6% benzyl chlorooxalate in 10 mL of MTBE over a period of 10–15 minutes. A solid, pyridinium chloride, formed shortly after the addition commenced. After the addition was completed the reaction mass was stirred for 60 minutes at 2° C. after which 10 mL of water was added and the reaction mass was stirred an additional 10 minutes at 3°–4° C. The aqueous layer was then separated and the organic layer was washed three times with 35 mL of aqueous 5% HCl solution and then twice with 75 mL portions of water. The product solution was dried over 5% by weight of anhydrous MgSO$_4$, and, after separation of the spent desiccant by filtration, the solvent was removed in vacuo leaving 6.2 g of white solid (61.4% of theory, uncorrected) that had a melting point of 60°–61° C. An IR spectrum of the product as a nujol mull showed no significant OH band in the 3500 cm$^{-1}$ region. A major monoperoxyoxalate carbonyl band was present at 1785 cm$^{-1}$ and a major oxalate carbonyl band was present at about 1740 cm$^{-1}$. The product had a rapid heat test result of 72° C. which confirmed that the product was a very low temperature peroxide. The product contained 6.14% active oxygen (theory, 6.37%) according to a peroxyester active oxygen method, therefore, the assay of the product was 96.4% and the corrected yield was 59.2%.

Based on the method of preparation, yield data, rapid heat test data and infrared spectral data the product obtained in this reaction was the desired title product.

Example 9

Preparation of 2,5-Dimethyl-2,5-di (t-butoxycarbonylcarbonylperoxy) hexane (I-9)

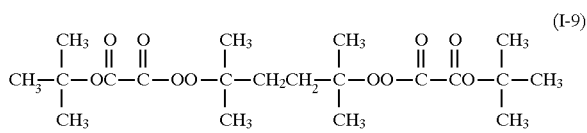

In this example the product was prepared in two synthetic steps. In the first step t-butyl alcohol was reacted with 50% molar excess of oxalyl chloride. Upon completion of the reaction the excess oxalyl chloride was stripped from the product at reduced pressure to produce t-butyl chlorooxalate having an assay of 100% and in a corrected yield of 90.8%. In the second step t-butyl chlorooxalate was reacted with 2,5-dimethyl-2,5-dihydroperoxyhexane, in the presence of pyridine, to yield the product as described below:

A 250 mL 3-neck flask, equipped with a magnetic stirring, a condenser, a thermometer and an addition funnel, and cooled with an ice-water bath, was charged with 60 mL of MTBE, 3.6 g (20.0 mmoles) of 98% 2,5-dimethyl-2,5-dihydroperoxyhexane and 4.5 g (57.0 mmoles) of pyridine. The stirred mixture was cooled to 0° C. and to it was slowly added a solution of 6.9 g (42.0 mmoles) of 100% t-butyl chlorooxalate in 10 mL of MTBE over a period of 10–15 minutes. A solid, pyridinium chloride, formed shortly after the addition commenced. After the addition was completed the reaction mass was stirred for 60 minutes at 2° C. after which 10 mL of water was added and the reaction mass was stirred an additional 10 minutes at 3°–4° C. The aqueous layer was then separated and the organic layer was washed three times with 35 mL of aqueous 5% HCl solution and then twice with 75 mL portions of water. The product solution was dried over 5% by weight of anhydrous MgSO$_4$, and, after separation of the spent desiccant by filtration, the solvent was removed in vacuo leaving 4.5 g (51.7% of theory, uncorrected) of a liquid product. An IR spectrum of the product showed no significant OH band in the 3500 cm$^{-1}$ region. A major monoperoxyoxalate carbonyl band was present at 1785 cm$^{-1}$ and a major oxalate carbonyl band was present at about 1740 cm$^{-1}$. The product had a rapid heat test result of 33° C. which confirmed that the product was an extremely low temperature peroxide.

Based on the method of preparation, rapid heat test data and infrared spectral data the product obtained in this reaction was the desired title product.

Example 10

Preparation of 2,5-Dimethyl-2,5-di(hexafluoro-amyloxycarbonylcarbonylperoxyyl)exane (I-10)

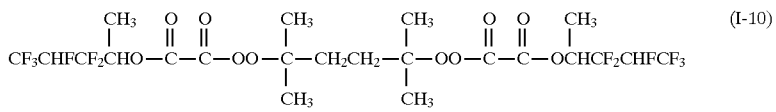

(I-10)

In this example the product was prepared in two synthetic steps. In the first step hexafluoroamyl alcohol was reacted with 100% molar excess of oxalyl chloride. Upon completion of the reaction the excess oxalyl chloride was stripped from the product at reduced pressure to produce hexafluoroamyl chlorooxalate having an assay of 91.3% and in a corrected yield of 52.8%. In the second step hexafluoroamyl chlorooxalate was reacted with 2,5-dimethyl-2,5-dihydroperoxyhexane, in the presence of pyridine, to yield the product as described below:

A 250 mL 3-neck flask, equipped with a magnetic stirring, a condenser, a thermometer and an addition funnel, and cooled with an ice-water bath, was charged with 60 ML of MTBE, 1.8 g (10.0 mmoles) of 98% 2,5-dimethyl-2,5-dihydroperoxyhexane and 2.3 g (29.0 mmoles) of pyridine. The stirred mixture was cooled to 0° C. and to it was slowly added a solution of 6.6 g (21.0 mmoles) of 91.3% hexafluoroamyl chlorooxalate in 10 mL of MTBE over a period of 10–15 minutes. After the addition was completed the reaction mass was stirred for 60 minutes at 2° C. after which 10 mL of water was added and the reaction mass was stirred an additional 10 minutes at 3°–4° C. The aqueous layer was then separated and the organic layer was washed three times with 35 mL of aqueous 5% HCl solution and then twice with 75 mL portions of water. The product solution was dried over 5% by weight of anhydrous $MgSO_4$, and, after separation of the spent desiccant by filtration, the solvent was removed in vacuo leaving 5.5 g (80.9% of theory, uncorrected) of a liquid product. An IR spectrum of the product showed a major monoperoxyoxalate carbonyl band at 1785 $cm^{-1}$ and a major oxalate carbonyl band at about 1755 $cm^{-1}$. The product had a rapid heat test result of 90° C. indicating that the product was a low temperature peroxide. The product contained 3.64% active oxygen (theory, 4.72%) according to a peroxyester active oxygen method, therefore, the assay of the product was 77.1% and the corrected yield was 62.4%.

Based on the method of preparation, yield data, rapid heat test data and infrared spectral data the product obtained in this reaction was the desired title product.

Example 11

Preparation of 2,5-Dimethyl-2,5-di (chlorocarbonylcarbonylperoxy)hexane (I-11)

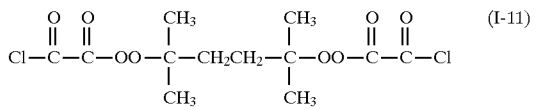

A 250 mL 3-necked flask equipped with a magnetic stirring bar, a condenser, a thermometer and an addition funnel and cooled with an ice bath was charged with 12.7 g (0.100 mole) of oxalyl chloride and 60 mL of MTBE. The flask contents were cooled to 0° C. Then to the resulting vigorously stirred solution at about 0° C. was slowly added 3.6 g (0.020 mole) of dry 98% 2,5-dimethyl-2,5-dihydroperoxyhexane in portions over a period of 20 minutes. The reaction was then stirred for an additional 3 hours at 0° C. Then 7.2 g of diglyme was added to the product solution and the solvent and excess oxalyl chloride were removed removed in vacuo leaving 15.6 g (>100% of theory, uncorrected) of a solution of the product (about 50% concentration) in diglyme. An IR spectrum of the product solution showed a major peroxyoxalate carbonyl band at 1790 $cm^{-1}$. The product solution had a rapid heat test result of 54°–57° C. indicating that the product was a very low temperature peroxide.

Based on the method of preparation, yield data, rapid heat test data and infrared spectral data the product obtained in this reaction was the desired title product.

Example 12

Preparation of 2,5-Dimethyl-2,5-di(t-butylperoxycarbonylcarbonylperoxy)hexane (I-12)

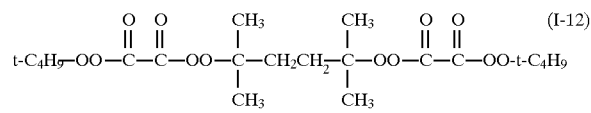

In this example the product was prepared in two synthetic steps. In the first step t-butyl hydroperoxide was reacted with 100% molar excess of oxalyl chloride to form t-butylperoxy chlorooxalate (A-1).

In the second step t-butylperoxy chlorooxalate (A-1) was reacted with 2,5-dimethyl-2,5-dihydroperoxyhexane in the presence of pyridine to yield the product (I-12).

A 125 mL flask was charged with 9.3 g (100 mmoles) of 97% t-butyl hydroperoxide, 75 mL of pentane and 3 g of anhydrous $MgSO_4$ at room temperature. The contents were stirred for 30 minutes after which the contents were filtered and the spent dessicant was washed with 25 mL of pentane and the pentane washings were combined with the filtrate. A 3-neck flask equipped with a magnetic stirring bar, a condenser, a thermometer and an addition funnel and cooled with a ice-water bath was then charged with 25.4 g (200 mmoles) of oxalyl chloride and 25 mL of pentane. The solution was cooled to 0° C. Then the dry pentane solution of t-butyl hydroperoxide was added slowly to the stirred oxalyl chloride/pentane solution over a period of 60 minutes at 0° C. The reaction was stirred for an additional 3 hours at 0° C. Then the pentane and excess oxalyl chloride were removed by stripping at ice-water temperature, leaving 18.5 g (>100% of theory, uncorrected; theoretical yield=18.1g) of a liquid product. An IR spectrum of the product showed a very slight OH band in the 3500 $cm^{-1}$ region and a single, major monoperoxyoxalate carbonyl band at 1797 $cm^{-1}$. The product had a rapid heat test result of 45° C. (very loud pop) which confirmed that the product, t-butylperoxy chlorooxalate, was a very low temperature peroxide. Impact shock testing [J. Varjavandi and O. L. Mageli, *J. Chem. Ed.* 48, A451 (1971)] showed that the product was shock sensitive at 3 inches and not shock sensitive at one inch. Because of the product's thermal and shock sensitivities, it was diluted with an equal weight of diglyme prior to subsequent use. The diglyme-diluted product had a rapid heat test result of 60° C. (mild decomposition) and a shock sensitivity above 20 inches.

In the second step, a 250 mL 3-necked flask equipped with a magnetic stirring bar, a condenser, a thermometer and an addition funnel and cooled with an ice bath was charged with 1.8 g (10.0 mmoles) of 98% 2,5-dimethyl-2,5-dihydroperoxyhexane (dry Luperox 2,5—2,5), 2.3 g (29.0 mmoles) of dry pyridine and 60 mL of MTBE. The flask contents were cooled to 0° C. Then to the resulting vigorously stirred solution at 0° C. was slowly added a solution of 7.7 g (21.0 mmoles) of about a 50% diglyme solution of t-butylperoxy chlorooxalate in 10 mL of MTBE. After the addition was completed the reaction mass was stirred for 60 minutes at 0° C. after which 10 mL of water was added and the reaction mass was stirred an additional 20 minutes at 0°–5° C. The aqueous layer was then separated and the organic layer was washed three times with 35 mL portions of aqueous 5% HCl solution and then twice with 75 mL portions of aqueous 5% NaHCO$_3$ solution. The product solution was dried over 5% by weight of anhydrous MgSO$_4$, and, after separation of the spent desiccant by filtration, 4.7 g of diglyme was added as a high-boiling safety diluent and the solvent was removed in vacuo leaving 8.7 g (>100% of theory, uncorrected; theoretical pure yield=4.7 g) of a fine slurry of the product in diglyme. An IR spectrum of the product solution showed two major peroxyoxalate carbonyl bands at 1769 cm$^{-1}$ and 1801 cm$^{-1}$. The product in diglyme had a rapid heat test result of 51° C. indicating that the product was a very low temperature peroxide.

Based on the method of preparation, yield data, rapid heat test data and infrared spectral data the product obtained in this reaction was the desired title product.

Example 13

Preparation of 2,5-Dimethyl-2,5-di(3-t-butyl-peroxy-1,3-dimethylbutoxycarbonylcarbonyl-peroxv)hexane (I-13)

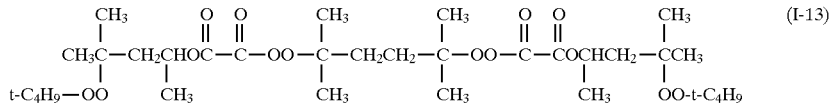

In this example the product was prepared in two synthetic steps. In the first step 3-t-butylperoxy-1,3-dimethylbutanol was reacted with 100% molar excess of oxalyl chloride. Upon completion of the reaction the excess oxalyl chloride was stripped from the product at reduced pressure to produce 3-t-butylperoxy-1,3-dimethylbutyl chlorooxalate having an assay of 97.5% and in a corrected yield of 98.5%. In the second step 3-t-butylperoxy-1,3-dimethylbutyl chlorooxalate was reacted with 2,5-dimethyl-2,5-dihydroperoxyhexane, in the presence of pyridine, to yield the product as described below:

A 250 mL 3-necked flask equipped with a magnetic stirring bar, a condenser, a thermometer and an addition funnel and cooled with an ice bath was charged with 1.6 g (9 mmoles) of dry 98% 2,5-dimethyl-2,5-dihydroperoxyhexane, 2.0 g (25 mmoles) of dry pyridine and 60 mL of MTBE. The flask contents were cooled to 0° C. Then to the resulting vigorously stirred solution at about 0° C. was slowly added a solution of 5.2 g (18 mmoles) of 97.5% 3-t-butylperoxy-1,3-dimethylbutyl chlorooxalate in 10 mL of MTBE. After the addition was finished, the reaction mass was stirred for 60 minutes at 2° C. after which 10 mL of water was added and the reaction mass was stirred an additional 10 minutes at 3°–4° C. The aqueous layer was then separated and the organic layer washed three times with 35 mL portions of aqueous 5% HCl solution and then twice with 75 mL portions of water. The product solution was dried over 5% by weight of anhydrous MgSO$_4$, and, after separation of the spent desiccant by filtration, the solvent was removed in vacuo leaving 6.5 g (>100% of theory, uncorrected) of a liquid product. An IR spectrum of the product showed no OH band in the 3500 cm$^{-1}$ region, a major monoperoxyoxalate carbonyl band at about 1790 cm$^{-1}$ and a major oxalate carbonyl band at about 1740 cm$^{-1}$. The product had a rapid heat test result of 54°–57° C. which confirmed that the product was a very low temperature peroxide. The product contained 3.84% active oxygen (theory, 4.80%) according to a peroxyester active oxygen method, therefore, the assay of the product was 80.0% and the corrected yield was 86.76%.

Based on the method of preparation, yield data, rapid heat test data and infrared spectral data the product obtained in this reaction was the desired title product.

Example 14

140° F. (60° C.) SPI Exotherm Data for 2,5-dimethyl-2,5-di (isobornyloxycarbonylcarbonylperoxy) hexane (I-4)

The unsaturated polyester resin composition employed in this example was a mixture of an unsaturated polyester and styrene monomer. The unsaturated polyester was an alkyd resin made by esterifying the following components:

| COMPONENT | QUANTITY (MOLES) |
|---|---|
| Maleic Anhydride | 1.0 |
| Phthalic Anhydride | 1.0 |

-continued

| COMPONENT | QUANTITY (MOLES) |
|---|---|
| Propylene Glycol | 2.2 |

0.013% by weight of hydroquinone inhibitor was added to the resulting resin. The alkyd resin had an Acid No. of 45–50. Seven (7) parts by weight of the above unsaturated polyester alkyd resin were diluted with three (3) parts by weight of styrene monomer. The resulting unsaturated polyester resin composition had the following properties:

Viscosity (Brookfield No. 2 at 20 r.p.m.)—13.0 poise

Specific Gravity—1.14

Gelation and cure characteristics of di(4-t-butylcyclohexyl) peroxydicarbonate (A-1), (a commercial peroxide product used to cure unsaturated polyester resin compositions), t-butyl peroxyneodecanoate (A-2), (another commercial peroxide product used to cure unsaturated polyester resin compositions), α-cumyl peroxyneodecanoate (A-3) (a commercial low temperature peroxide initiator) and 2,5-dimethyl-2,5-di(isobornyloxycarbonylcarbonylperoxy)-hexane (I-4), a novel bis(monoperoxyoxalate) composition of the instant invention, were determined using the Standard SPI Exotherm Procedure (Suggested SPI Procedure for Running Exotherm Curves-Polyester Resins, published in the Preprint of the 24th Annual Technical Conference—Reinforced Plastics/Composites Division, Society of the Plastics Industry, Inc., 1969). Using this procedure at 140° F. (60° C.), A-1, A-2, A-3 and I-4 were comparatively evaluated. The level of I-4 was 1.0 g per 100 g of resin on a pure basis and the levels of A-1, A-2 and A-3 (per 100 g of resin) were equivalent in active oxygen content to a 1.0 g level of I-4 (pure basis). The results of this investigation are given in Example 14 Table and show that I-4 gelled and cured the resin much more rapidly than A-1, A-2 and A-3, hence, I-4, a novel bis(monoperoxyoxalate) composition of the instant invention, was much more active in curing the unsaturated polyester resin than were three of the lowest temperature, commercial peroxide catalysts.

EXAMPLE 14 TABLE
140° F. (60° C.) SPI EXOTHERM DATA

| CURING AGENT | G/100 G RESIN | GEL, MINS. | CURE, MINS. | PEAK EXO, °F. | BARCOL HARDNESS |
|---|---|---|---|---|---|
| I-4 | 1.0 | 2.2 | 3.6 | 3.08 | 35–40 |
| A-1 | 1.29 | 8.5 | 11.4 | 317 | 35–40 |
| A-2 | 0.82 | 10.5 | 13.8 | 328 | 35–40 |
| A-3 | 1.03 | 5.8 | 7.7 | 316 | 35–40 |

The subject matter regarded by the applicant as his invention is particularly pointed out and distinctly claimed as follows:

I claim:

1. A novel bis(mono- or diperoxyoxalate) of Structure A:

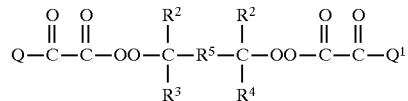

where $R^1$, $R^2$, $R^3$ and $R^4$ are the same or different and are alkyl groups of 1 to 4 carbons, $R^5$ is a group selected from —(CH$_2$)$_n$—, where n is 1 to 6, —C≡C—, —C≡C—C≡C—, 1,4-phenylene, substituted or unsubstituted 1,3-phenylene, the substituent being the structure,

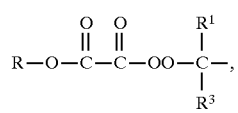

Q and $Q^1$ are independently selected from the group consisting of chloro, bromo, R—O, and $R^6$—OO, where R is selected from the group consisting of H, a substituted or unsubstituted alkyl group of 1 to 24 carbons, substituents being one or more alkyl groups of 1 to 6 carbons, alkoxy groups of 1 to 6 carbons, aryloxy groups of 6 to 10 carbons, fluoro, chloro, bromo, carboxy and cyano, a substituted or unsubstituted alkenyl group of 3 to 12 carbons, substituents being one or more lower alkyl groups of 1 to 4 carbons, a substituted or unsubstituted aryl group of 6 to 10 carbons, substituents being one or more alkyl groups of 1 to 6 carbons, alkoxy groups of 1 to 6 carbons, aryloxy groups of 6 to 10 carbons, chloro, bromo and cyano, a substituted or unsubstituted aralkyl group of 7 to 13 carbons, substituents being one or more alkyl groups of 1 to 6 carbons, a substituted or unsubstituted cycloalkyl group of 5 to 12 carbons, a substituted or unsubstituted cycloalkyl group of 5 to 12 carbons having one or more oxygen or nitrogen atoms in the cycloalkane ring, with substituents for the cycloalkyl group being one or more lower alkyl groups of 1 to 4 carbons, a substituted or unsubstituted bicycloalkyl group of 6 to 14 carbons, with substituents being one or more lower alkyl groups of 1 to 4 carbons, a substituted or unsubstituted tricycloalkyl group of 7 to 16 carbons, with substituents being one or more lower alkyl groups of 1 to 4 carbons, and, R can additionally be structure (a),

where $R^{10}$ is an unsubstituted alkylene group of 1 to 3 carbons or a substituted alkylene group of 1 to 3 carbons, substituents being one or more lower alkyl groups of 1 to 4 carbons, $R^7$ and $R^8$ are alkyl groups of 1 to 4 carbons, $R^9$ is selected from unsubstituted t-alkyl groups of 4 to 12 carbons, substituted t-alkyl groups of 4 to 12 carbons, t-cycloalkyl groups of 6 to 13 carbons, t-alkynyl groups of 5 to 9 carbons, t-aralkyl groups of 9 to 13 carbons, unsubstituted aroyl groups of 7 to 11 carbons, substituted aroyl groups of 7 to 11 carbons, where the substituent for the t-alkyl groups is a t-alkylperoxy group of 4 to 8 carbons and the substituents for the aroyl groups are one or more lower alkyl groups of 1 to 4 carbons, alkoxy groups of 1 to 4 carbons, phenyl groups, acyloxy groups of 2 to 8 carbons, t-alkylperoxycarbonyl groups of 5 to 9 carbons, fluoro, chloro or bromo, and $R^9$ can also be structures (b), (c) and (d)

where x is 0 or 1, $R^{11}$ is a substituted or unsubstituted alkyl group of 1 to 18 carbons, substituents being one or more alkyl groups of 1 to 6 carbons, t-alkylperoxy groups of 4 to 8 carbons, alkoxy groups of 1 to 6 carbons, aryloxy groups of 6 to 10 carbons, hydroxy, chloro, bromo or cyano or a substituted or unsubstituted cycloalkyl group of 5 to 12 carbons or substituted or unsubstituted cycloalkyl groups of 5 to 12 carbons having one or more oxygen or nitrogen atoms in the cycloalkane ring, with substituents for the cycloalkyl groups being one or more lower alkyl groups of 1 to 4 carbons, and, $R^{12}$ is selected from a substituted or unsubstituted alkylene group of 2 to 3 carbons, substituents being one or more lower alkyl groups of 1 to 4 carbons, or a substituted or unsubstituted 1,2-, 1,3- or 1,4-phenylene group, substituents being one or more lower alkyl groups of 1 to 4 carbons, chloro, bromo, nitro or carboxy, and, $R^{13}$ is a lower alkyl group of 1 to 4 carbons, and, additionally, the two $R^{13}$ groups may be concatenated to form an alkylene group of 4 to 5 carbons, $R^{14}$ is a lower alkyl group of 1 to 4 carbons, $R^{15}$, $R^{16}$ and $R^{17}$ are selected from hydrogens, alkyl groups of 1 to 8 carbons, aryl groups of 6 to 10 carbons, alkoxy groups of 1 to 8 carbons and aryloxy groups of 6 to 10 carbons, and, $R^6$ is selected from an unsubstituted t-alkyl group of 4 to 12 carbons, a substituted t-alkyl group of 4 to 12 carbons, a t-cycloalkyl group of 6 to 13 carbons, a t-alkynyl group of 5 to 9 carbons, and a t-aralkyl group of 9 to 13 carbons, where the substituent for the t-alkyl group is a t-alkylperoxy group of 4 to 8 carbons.

2. The bis(mono- or diperoxyoxalate) compound as defined in claim 1 selected from the group consisting of: 2,5-dimethyl-2,5-di(ethoxycarbonylcarbonylperoxy) hexane, 2,5-dimethyl-2,5-di(docosyloxycarbonylcarbonylperoxy)hexane, 2,5-dimethyl-2,5-di(4-t-butylcyclohexoxycarbonylcarbonyl-peroxyl hexane, 2,5-dimethyl-2,5-di(isobornyloxycarbonylcarbonylperoxy)hexane, 2,5-dimethyl-2,5-di(neopentyloxycarbonylcarbonylperoxy) hexane, 2,5-dimethyl-2,5-di(neopentyloxycarbonylcarbonylpercoxy)-3-hexyne, 2,5-dimethyl-2,5-di(bornyloxycarbonylcarbonylperoxy)hexane, 2,5-dimethyl-2,5-di(benzyloxycarbonylcarbonylperoxy) hexane, 2,5-dimethyl-2,5-di(t-butoxycarbonylcarbonylperoxy) hexane, 2,5-dimethyl-2,5-di(hexafluoroamyloxycarbonylcarbonylperoxy)hexane, 2,5-dimethyl-2,5-di(chlorocarbonylcarbonylperoxy)hexane, 2,5-dimethyl-2,5-di(t-butylperoxycarbonylcarbonylperoxy) hexane, and 2,5-dimethyl-2,5-di(3-t-butylperoxy-1,3-dimethylbutoxy-carbonylcarbonylperoxy)hexane.

3. The bis(mono- or diperoxyoxalate) as defined in claim 1 wherein Q and $Q^1$ are the same and $R^1$, $R^2$, $R^3$ and $R^4$ are the same and are alkyl groups of 1 to 2 carbons.

4. The bis(mono- or diperoxyoxalate) as defined in claim 3 wherein Q and $Q^1$ are selected from R—O and Cl.

5. The bis(mono- or diperoxyoxalate) as defined in claim 4 wherein Q and $Q^1$ are R—O.

6. The bis(mono- or diperoxyoxalate) as defined in claim 5 wherein $R^5$ is selected from —C≡C— and —$(CH_2)_n$—, and n is 2.

7. The bis(mono- or diperoxyoxalate) as defined in claim 6 wherein $R^5$ is —$(CH_2)_n$— and n is 2.

8. The bis(mono- or diperoxyoxalate) as defined in claim 7 wherein R is selected from the group consisting of H, a substituted or unsubstituted alkyl group of 1 to 22 carbons, substituents being one or more alkyl groups of 1 to 6 carbons, alkoxy groups of 1 to 6 carbons, aryloxy groups of 6 to 10 carbons, chloro, bromo, carboxy and cyano, a substituted or unsubstituted cycloalkyl group of 5 to 12 carbons, substituents being one or more lower alkyl groups of 1 to 4 carbons, a substituted or unsubstituted bicycloalkyl group of 6 to 14 carbons, with substituents being one or more lower alkyl groups of 1 to 4 carbons, and structure (a).

9. A process for the curing of unsaturated polyester resin compositions which comprises heating such resins in the presence of initiating amounts of the bis(mono- or diperoxyoxalate) of claim 1 at appropriate temperatures.

10. The process as defined in claim 9 wherein the bis (monoperoxyoxalate) is 2,5-dimethyl-2,5-di (isobornyloxycarbonylcarbonylperoxy)hexane.

11. A process for polymerizing ethylenically unsaturated monomers which comprises heating such monomers in the presence of initiating amounts of the bis(mono- or diperoxyoxalate) of claim 1 at appropriate temperatures.

12. The process as defined in claim 11 wherein the ethylenically unsaturated monomer is vinyl chloride.

* * * * *